(12) United States Patent
Dickson et al.

(10) Patent No.: US 7,243,559 B2
(45) Date of Patent: *Jul. 17, 2007

(54) EXHAUST GAS PARTICULATE MEASURING SYSTEM

(75) Inventors: Richard R. Dickson, Peoria, IL (US); Russell R. Graze, Jr., Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 206 days.

This patent is subject to a terminal disclaimer.

(21) Appl. No.: 10/692,871

(22) Filed: Oct. 24, 2003

(65) Prior Publication Data

US 2004/0118223 A1 Jun. 24, 2004

Related U.S. Application Data

(62) Division of application No. 09/905,698, filed on Jul. 10, 2001.

(51) Int. Cl.
*G01N 1/00* (2006.01)

(52) U.S. Cl. .................. 73/863.01; 73/863.03

(58) Field of Classification Search ............ 73/863.02, 73/863.01, 863.03, 23.31, 31.03, 863.81
See application file for complete search history.

(56) References Cited

U.S. PATENT DOCUMENTS

| | | | | |
|---|---|---|---|---|
| 3,699,814 A | * | 10/1972 | Kaufman | ................. 73/863.11 |
| 5,058,440 A | * | 10/1991 | Graze, Jr. | ................. 73/863.83 |
| 5,546,788 A | * | 8/1996 | Dickow | ................. 73/28.01 |
| 6,021,678 A | | 2/2000 | Vardiman et al. | |
| 6,138,708 A | * | 10/2000 | Waldbusser | ................. 137/341 |
| 6,615,677 B2 | * | 9/2003 | Dickson et al. | ........... 73/863.01 |
| 2003/0136177 A1 | * | 7/2003 | Hendren et al. | ............ 73/23.31 |
| 2004/0191130 A1 | * | 9/2004 | Marek et al. | ................. 422/109 |
| 2005/0056079 A1 | * | 3/2005 | Nagy et al. | .................. 73/1.07 |

FOREIGN PATENT DOCUMENTS

JP 09159586 A * 6/1997

* cited by examiner

*Primary Examiner*—Hezron Williams
*Assistant Examiner*—Nashmiya Fayyaz
(74) *Attorney, Agent, or Firm*—Jeff A. Greene

(57) ABSTRACT

A gas sampling system 36 capable of testing and certifying internal combustion engines 16 under transient conditions is provided and includes a partial flow dilution tunnel 38, master and slave mass flow controllers 80,60 and a transient dilution air flow controlling arrangement 110. The transient dilution air flow controlling arrangement 110 measures the transient changes in intake air and varies the flow of diluent air to the partial flow dilution tunnel 38. By controlling the diluent air in this manner ensures that a particle sample can be taken at any time that is at a constant proportion to the exhaust flow rate.

37 Claims, 5 Drawing Sheets

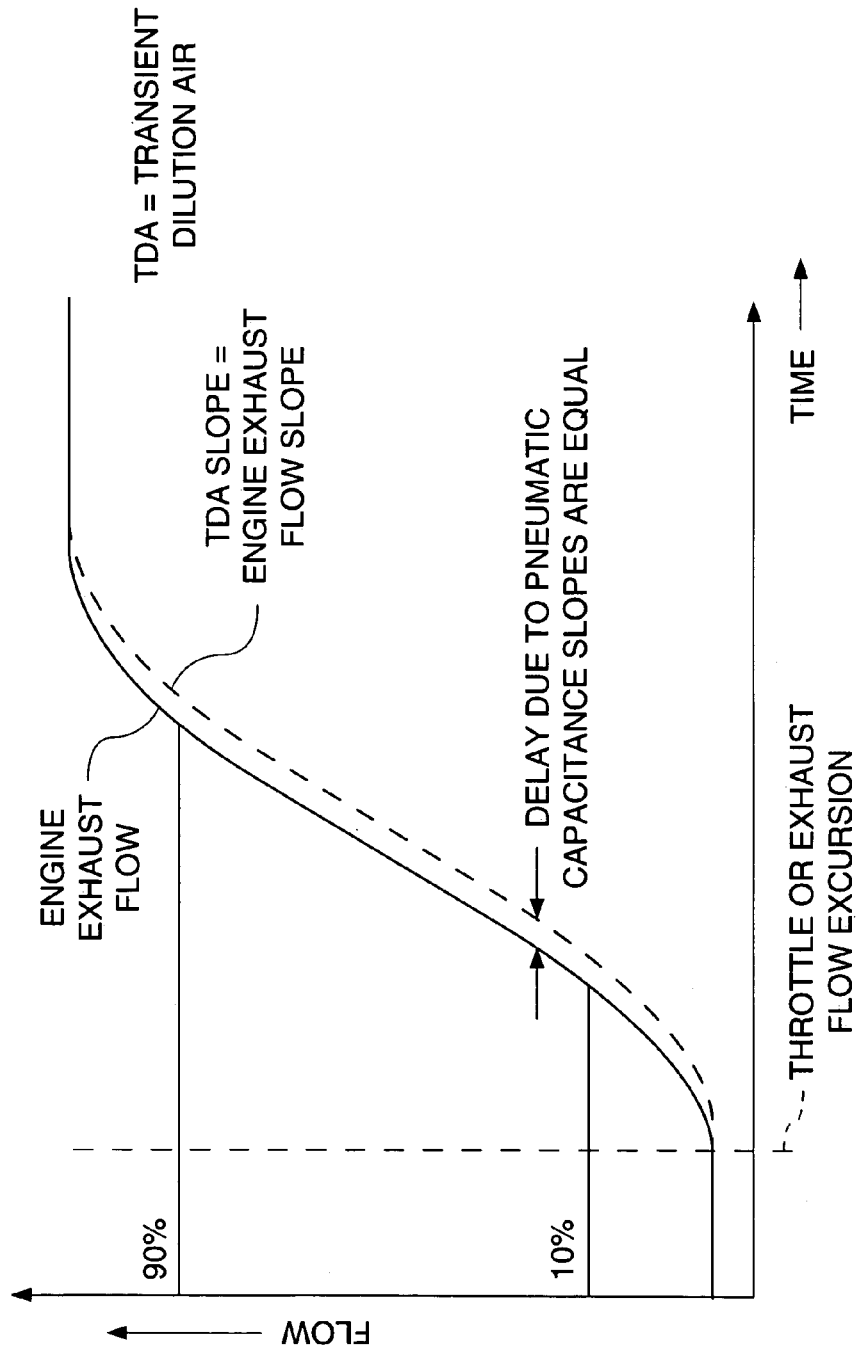

EXHAUST GAS PARTICULATE MEASURING SYSTEM

This is a divisional of copending application Ser. No. 09/905,698, filed Jul. 10, 2001.

TECHNICAL FIELD

The invention relates to a system for measuring particulate matter in the exhaust gas stream of an internal combustion engine, and more particularly to a partial flow dilution sampling system for measuring the particulate matter during transient engine conditions.

BACKGROUND

Exhaust gas sampling systems that utilize partial flow dilution tunnels (PFDT) have been used since the early 1990's as an effective alternative to full dilution tunnels systems for development and certification of engines where steady-state model testing was permitted. Previously, all off-highway and until recently, much of European-bound on-highway engine testing and certification was performed with systems utilizing PFDT's, due to the fact that they are more portable, cheaper and more repeatable than their full dilution counterparts. Regulatory organizations such as ISO, CARB, EPA and EEC all permit the use of PFDT's for steady state test cycle certification. One such system is disclosed in U.S. Pat. No. 5,058,440 issued on Oct. 22, 1991 to Russell R. Graze and is assigned to the owner of the present application.

The Environmental Protection Agency has declared its interest in promulgating transient cycle regulations of large off-highway diesel engines in order to better control particulate emissions output from these engines. These regulations are expected to be in effect by 2006. The size of the off-highway diesel engines to be regulated eclipses the mass flow rate capacity of the industry's full dilution tunnels that have been in use for the past twenty plus years to quantify on-highway engine emission levels including particulate matter (PM). Furthermore, the sheer number of off-highway ratings to be developed, in combination with concurrent regulatory pressures placed on on-highway engine development teams, preclude the use of existing full dilution tunnels for off-highway development even for small engines.

Therefore it is desirable to develop a PFDT that can be used to test and certify off-highway diesel engines under transient conditions and more than likely will be utilized to test on-highway engines under transient conditions as well. One such system is described in U.S. Pat. No. 6,062,092 issued to Christopher Weaver on May 16, 2000 and is assigned to Engine, Fuel, and Emissions Engineering, Incorporated. This system utilizes a feedback arrangement to change the proportion of exhaust gas being sampled based on changes in the exhaust flow from an engine. However, this system uses the pressure differential between the exhaust gas flow stream and the pressure inside a sampling probe for feedback to control the proportionality of the exhaust sample and diluent air in a dilution tunnel. This system uses the last possible point in a test system to check for excursions in engine gas flow to sample for test changes (i.e. the exhaust gas flow stream) and does not discuss or take into account the pneumatic capacitance of the system. Pneumatic capacitance is the resistance in the sampling system to react to changes in system under transient conditions. Additionally, the U.S. Pat. No. 6,062,092 prior art does not take into account particulate deposition which is caused by thermophoresis.

The present invention is directed to overcome one or more of the problems as set forth above.

SUMMARY OF THE INVENTION

In one aspect of the present invention, a transient dilution air control arrangement for controlling a dilution air supply to a partial flow dilution tunnel of a gas sampling system is provided. The partial flow dilution tunnel is connected to an exhaust pipe of an internal combustion engine. The gas sampling system has a first mass flow controller operatively connected to an inlet of the partial flow dilution tunnel, a second mass flow controller connected to an outlet end of the partial flow dilution tunnel and a filter interposed the second mass flow controller and the outlet end of the partial flow dilution tunnel. The transient dilution control arrangement includes a constant mass flow stream connected to the input of the partial flow dilution tunnel and a variable mass flow stream connected to the constant mass flow stream.

In yet another aspect of the present invention, a gas sampling system for measuring particulate matter in an exhaust gas stream of an internal combustion engine is provided. The gas sampling system includes a partial flow dilution tunnel connected to the exhaust gas stream of the engine. A first mass flow controller is operatively connected to an inlet of the partial flow dilution tunnel. A second mass flow controller is connected to an outlet end of the partial flow dilution tunnel; A transient dilution air control arrangement is interposed the first mass flow controller and the inlet of the partial flow dilution tunnel and controls a dilution air supply to the partial flow dilution tunnel.

BRIEF DESCRIPTION OF THE DRAWINGS

FIG. 5 is a graphical relationship between engine exhaust flow and transient dilution air response time.

DETAILED DESCRIPTION

Figure 1:
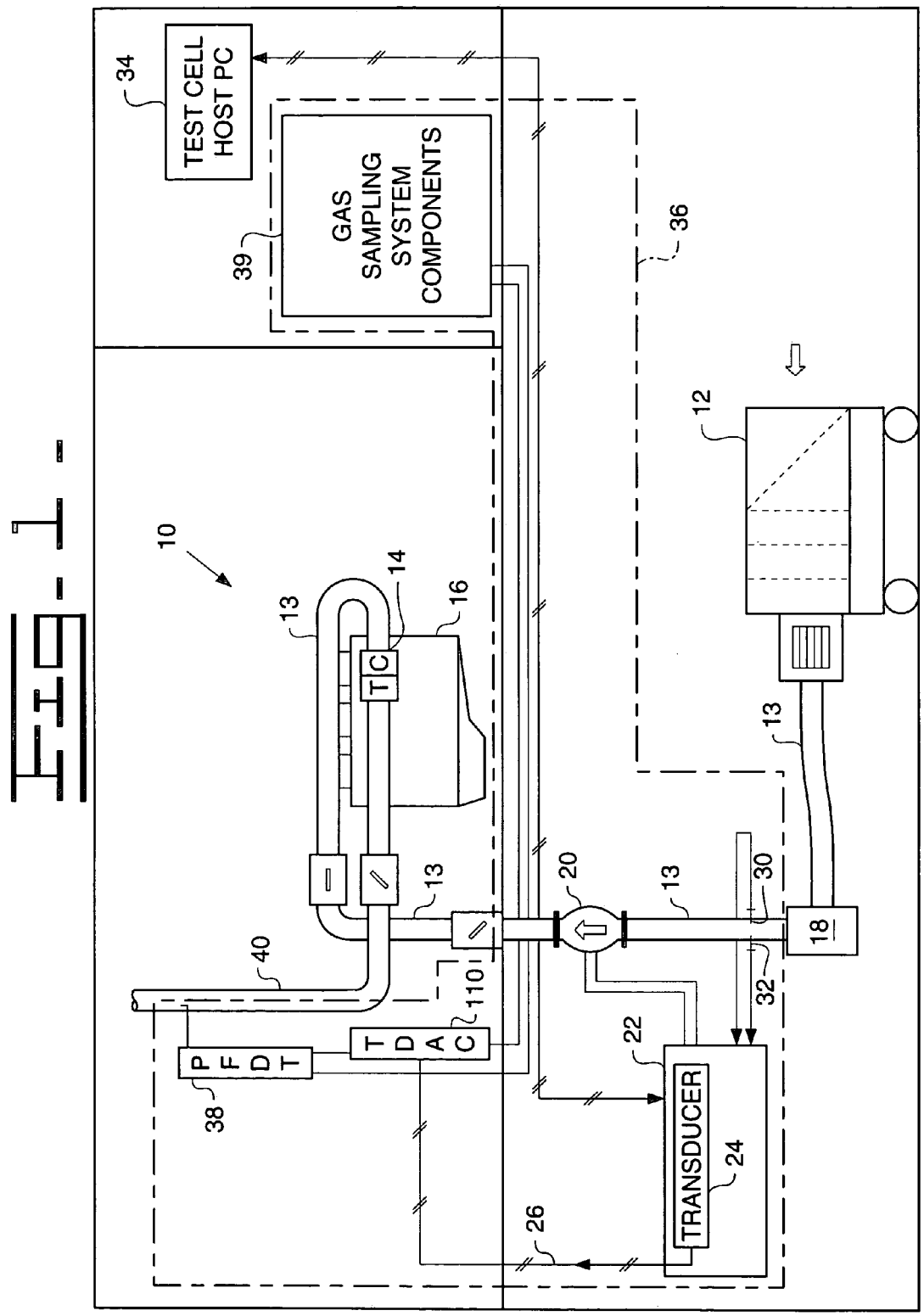
FIG. 1 is an overall diagrammatic view of an engine test cell.

As shown in FIG. 1, an engine test cell 10 is shown in accordance with the present invention includes a supply of intake air 12 connected as by conduit 13 to an air intake 14 of an internal combustion engine 16. Positioned in the conduit 13 between the supply of intake air 12 and the engine 16 is a filter 18, which may be a canister filter or any of a number of known filter arrangements.

A laminar flow element 20 or other flow device is positioned in conduit 13 between the filter 18 and the engine 16. Laminar flow element 20 is a pressure differential flow element located to measure the flow of intake air 14 to engine 16. Laminar flow element 20 is connected to an airflow rate transducer enclosure 22. Located in the enclosure 22 is a pressure differential transducer 24 that converts the pressure differential across laminar flow element 20 into, for example a 0-5 Vdc or other suitable range such as 0-10 Vdc, an analog signal output that is transmitted through conductor 26 for use as will be described later. It should be understood that the arrangement described above is for exemplary purposes and a non-linear measurement device such as a Brandt Air Flow Meter can be used if a linearizing algorithm is used or any other flow measurement system that produces a voltage output linear to flow rate is applicable. Also the test cell 10 shows an internal combustion engine 16 having only a single turbo charger. However, in the event that an engine 16 having a dual or quad turbo charger arrangement (not shown) is to be tested the supply of intake air 14 will be separated into two or four paths respectively, each of which will contain a laminar flow element 20 up stream of each turbo charger.

Additional measurements take place in the conduit 13 before the laminar flow element 20. A probe 30 to monitor the percent of relative humidity in the supply of intake air 14 is connected, as by wire, to the airflow rate transducer enclosure 22. A resistive temperature probe 32 is also connected by wire to the enclosure 22. These measurements taken are relayed to a test cell host computer 34.

Figure 2:
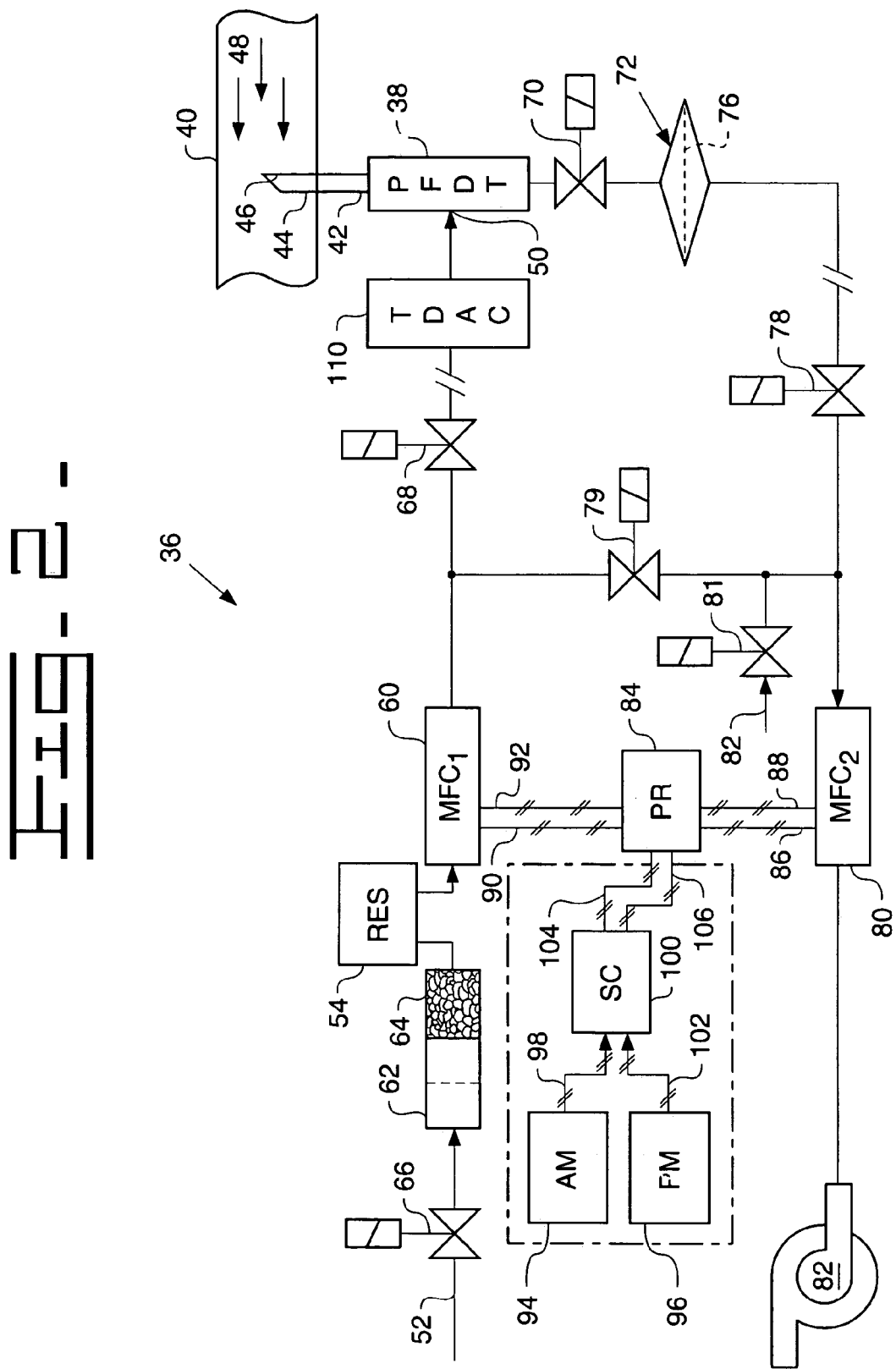
FIG. 2 is a diagrammatic view of a gas sampling system of embodying the present invention.

Referring now to FIGS. 1 and 2, a gas sampling system 36 constructed in accordance with the present invention includes a partial flow dilution tunnel (PFDT) 38. Dilution tunnel 38 is any type of known configurations that includes mixing box types or the type that includes a porous center tube having a plurality of micron-sized holes located in an air distribution tube positioned within an air supply chamber. The later type of which is disclosed in U.S. Pat. No. 5,058,440. Additionally, a plurality of additional control components 39 for the gas sampling system 36 are shown in more detail in FIG. 2 are connected to the outlet of dilution tunnel 38. Dilution tunnel 38 is connected to an exhaust pipe 40 of the engine 16. The dilution tunnel 38 can be connected to the exhaust pipe 40 in a low pressure section of the pipe 40 where excursions are minimized. Or optionally a sampling probe 42, such as an orifice-tipped sampling probe sized and designed to minimize the effect of pressure excursions in the exhaust pipe 16, is connected to one end or inlet of the dilution tunnel 38 extends within the exhaust pipe 40. Sampling probe 42 is known as a "square-root extractor" in the industry. Use of this sampling probe 42 gives the option of sampling upstream of a back pressure regulating device or in a conventional stack without the potential of data bias. As seen in FIG. 2 the probe has a nose portion 44 defining an inlet passage 46 projecting into the exhaust pipe 40. Thus, a proportionate sample of a particle-laden exhaust stream, as is indicated by the reference number 48, is directed into the dilution tunnel 38.

An inlet port 50 in the dilution tunnel 38 is in communication with a supply of air such a plant air supply, as is indicated generally by the reference number 52. In order to better regulate the flow rate of the diluent air into the dilution tunnel 38 the supply of air 52 is passed in serially arranged order to a pressurized clean air reservoir (Res) 54 and an electrically controlled, mass flow controller 60 (MFC1). Before reaching reservoir 54 the air is treated to improve its cleanliness, as by passing the supply of air 52 serially through a desiccant filter 62 to remove excess moisture and a charcoal scrubber 64 or the like to remove oil and/or hydrocarbons. A solenoid valve 66 is located upstream of filter 62 for turning on and off the supply of air 52. A solenoid valve 68 is connected down stream of the mass flow controller 60 and prior to the dilution tunnel 38.

The opposite or outlet end of the dilution tunnel 38 is connected to a solenoid valve 70 and a diagrammatically illustrated filter assembly 72. The filter assembly 72 also has a removable filter element 76 as is schematically indicated. The filter assembly 72 is connected in serial order to a solenoid valve 78, an electrically controlled, mass flow controller 80 (MFC2) and a vacuum pump 82. Additionally, connected in parallel to the outlet of the mass flow controller 60 and the inlet of the mass flow controller 80 is a solenoid valve 79. A solenoid valve 81 is connected between solenoid valve 79 and the inlet to the mass flow controller 80. Solenoid valve 81 has its inlet open to the atmosphere so that the vacuum pump 80 is not destroyed when the sampling system is not in operation. Solenoid valve 81 is equipped with a specially sized orifice 82 to allow standby operation in anticipation of sampling. The orifice 82 minimizes the pressure loss across the clean filter element 76 and the vacuum line.

The electrically controlled, mass flow controller (MFC2) 80 is the master controller and is used as a total flow rate controlling instrument, and the electrically controlled, mass flow controller (MFC1) 60 is the slave controller and is used as an instrument for precisely controlling the diluent airflow rate from the reservoir 54. These thermal mass flow controllers are preferably commercially available capillary tube-type and operate substantially independently of normal temperature and pressure variations. The master controller 80 and slave. controller 60 are respectively electrically connected to a microprocessor (PR) 84 by pairs of electrical lines 86,88 and 90,92 respectively.

As shown in FIG. 2 the previous system taught in U.S. Pat. No. 5,058,440, an air flow rate meter (AM) 94, such as a laminar flow element or a Brandt flow meter, which measures the rate of incoming air supplied to the engine 16 to be sampled. Also, a fuel flow rate meter (FM) 96 is provided to measure the rate of fuel being instantaneously supplied to the engine. The air flow rate meter 94 has a signal line 98 that is connected to a signal conditioner 100, and the fuel flow rate meter 96 has a signal line 102 connected also to the signal conditioner. The signal conditioner 100 preferably has two programmable electronic processing units therein, although not shown. One of these units is adaptable to convert the voltage signal in signal line 98 by a first preprogrammed rate table to an electrical signal in a first outlet line 104 to microprocessor (PR) 84, and the other unit is adaptable to convert the frequency signal in signal line 102 by a second pre-programn-ied rate table to an electrical signal in a second outlet line 106 to microprocessor 84.

Figure 3:
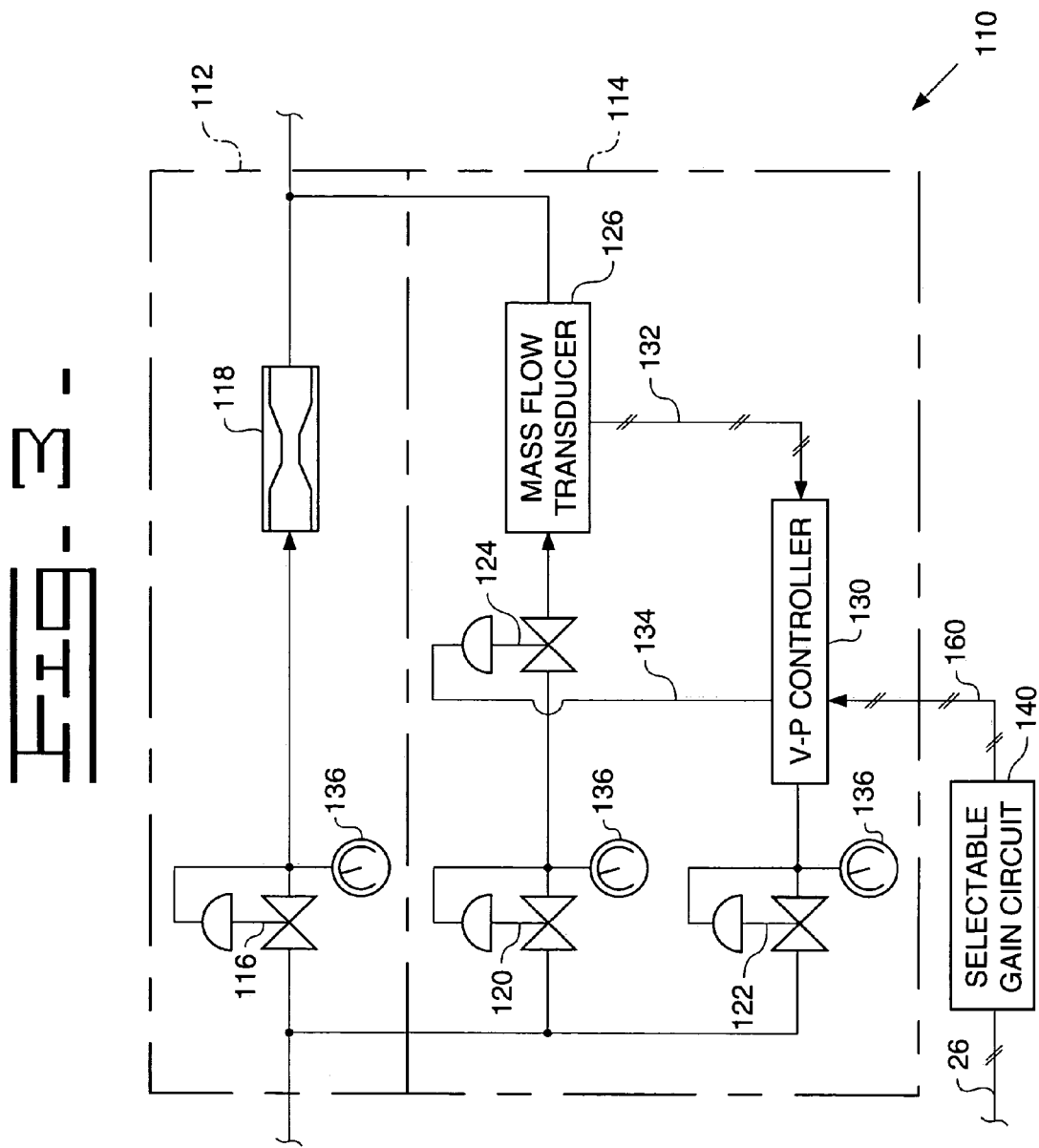
FIG. 3 is a diagrammatic view of a transient dilution air controller from FIG. 2.

Positioned in close proximity a predetermined distance from the dilution tunnel 38 is a transient dilution airflow control arrangement (TDAC) 110. Referring now to FIG. 3 the transient dilution air control arrangement 110 divided into a constant mass flow stream 112, which for exemplary purposes supplies a fixed flow of 130 liters per minute of diluent air for a given test and a variable mass flow stream 114, which for exemplary purposes supplies between 0 and 30 liters per minute of diluent air for a given test. The constant mass flow stream 112 is positioned downstream of slave mass flow controller 60 and includes a pressure regulating valve 116 that is serially operatively connected to a critical flow venturi 118. The critical flow venturi is manufactured of a material that is dimensionally stable under thermal excursions. Such material may be Invar 36, ceramic, jewel, or certain varieties of highly thermally stable stainless steel (particularly 400 series stainless steel).

The variable mass flow stream 114 is connected in parallel to the constant mass flow stream 112 and includes first and second parallel connected pressure regulating valves 120, 122. The first pressure regulating valve 120 is serially operatively connected to a dome loaded regulating valve 124 and a thermal mass flow transducer 126. The output of the thermal mass flow transducer 126 is operatively connected back to the output of the critical flow venturi 118. The second pressure regulating valve 122 is serially operatively connected to a voltage to pressure controller 130. An electrical output from the thermal mass flow transducer 126 is connected by a conductor 132 to the voltage to pressure controller 130. A conduit 134 connects the voltage to pressure controller 130 to the third pressure regulating valve 124. It should be understood that pressure regulating valve 116 and first and second pressure regulating valves 120,122 are shown as being manually operated valves with pressure indicating gages 136 for adjusting each to a desired pressure setting for a given test. However, it should be understood that it is considered to be within the understanding and scope of the present application that pressure regulating valve 116 and the first and second regulating valves 120,122 could be electrically controlled valves that are connected to and controlled by the microprocessor 84.

Figure 4:
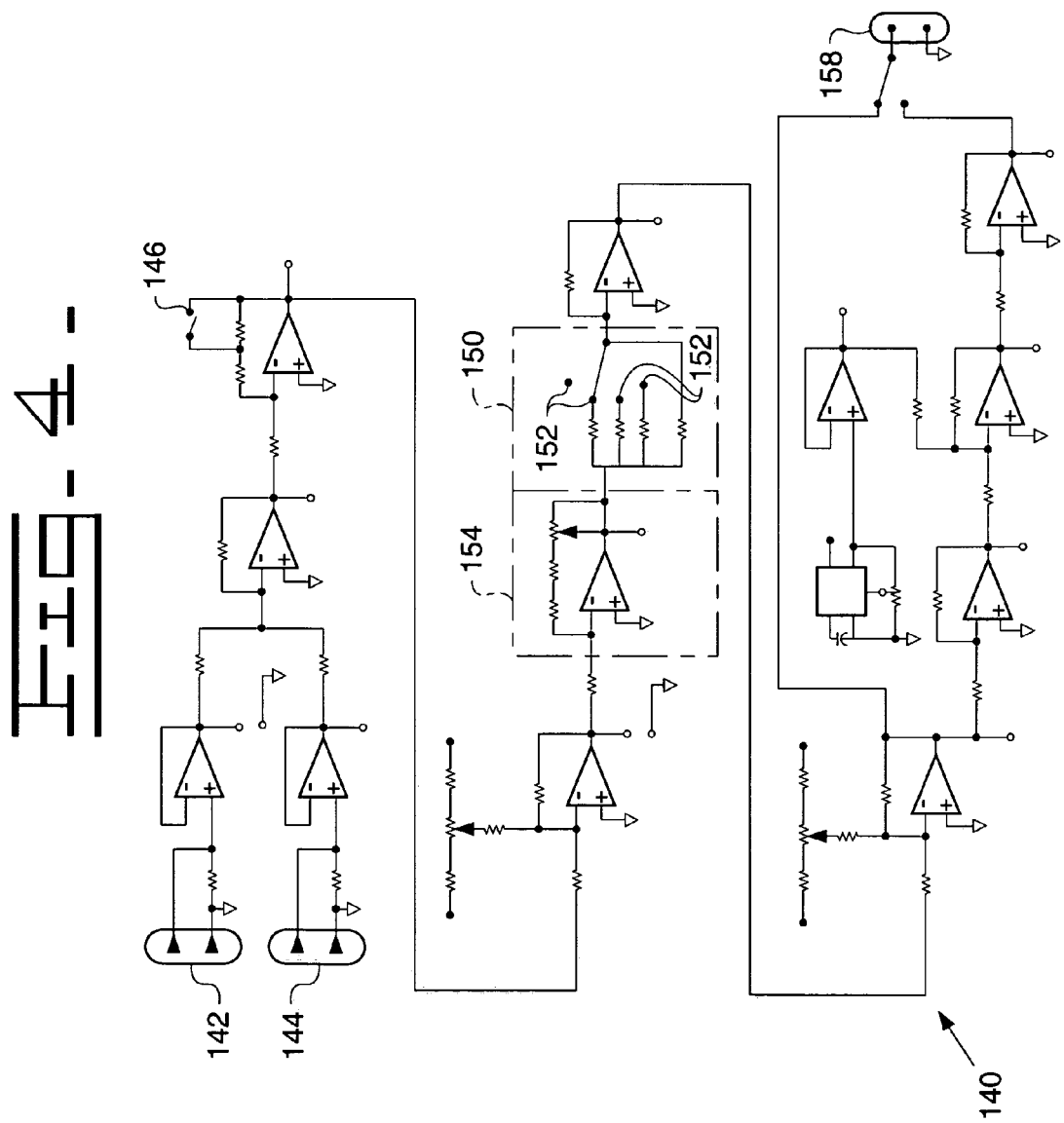
FIG. 4 is an electrical schematic for the transient dilution air controller of FIG. 3.

As seen in FIG. 3 and shown in detail in FIG. 4, a selectable gain circuit 140 is connected to the voltage to pressure controller 130 via conductor 160. The selectable gain circuit 140 is an analog refining circuit that receives an electrical input signalproportional to the mass flow rate of the intake air through conductor 26 from the pressure differential transducer 24. The analog signal from the pressure differential transducer 24 is received at a first input connection 142. In the event of a dual intake path fora dual turbo charged internal combustion engine 16 a second input connection 144 is provided. A switch 146 provides that the circuit 140 can be toggled between an open position for a single channel input or closed to average a dual channel input. A selectable gain switch 150 is selectable between a plurality of coarse voltage positions 152, for example from 0-5 Vdc maximum position to 0-1.67 Vdc minimum position, based on the amount of intake air or particular size of engine 16 for a given test, potentiometer 154 is used to fine tune the signal thereafter. A remaining portion 156 of circuit 140 refines the analog signal in a conventional manner with an output connection 158 supplying the analog signal to the voltage to pressure controller 130 via conductor 160. The selectable gain circuit 140 can be manually operated or can by controlled by the microprocessor 84.

Referring now to FIG. 5 a graph representing the relationship between engine exhaust flow and transient dilution air response time.

INDUSTRIAL APPLICABILITY

In operation, solenoid valves 66,68,70,78 and 81 are open/closed type valves that are used for many purposes, which are apparent by an inspection of FIG. 2, such as at start up and by pass mode so that the vacuum pump 82 is not damaged. Solenoid valve 79 is included to provide a calibration loop, which by shunting the system, places the slave mass flow controller (MFC1) 60 and the master mass flow controller (MFC2) 80 directly in series with one another.

The gas sampling system shown in FIGS. 1 and 2 uses capillary tube-type thermal mass flow controllers 60 and 80 are electrically driven by the microprocessor 84. The processor 84 controls the total air flow rate to the partial flow dilution tunnel 38 that is capable of re-acting to transient engine conditions while substantially eliminating particle deposition and entrainment. For example, the ratio-establishing processor 84 can apportion the control signals in the lines 86 and 88 to the master mass flow controller 80, and the control signals in the lines 90 and 92 to the lesser flow capacity slave mass flow controller 60 to establish an approximate ratio of flow of about 1.1 to 1.0, yielding a typical dilution ratio of about 10:1. This value should be controllable and variable.

Transient conditions are corrected for by the laminar flow element 20 the selectable gain circuit 140 and the transient dilution air control arrangement 110. Specifically, during a transient testing operation the laminar flow element 20 measures changes in the differential pressure across the element 20. This measurement is converted to an analog dc voltage signal by the pressure differential transducer 24. The selectable gain circuit 140 refines the analog signal as previously discussed. The transient dilution air control arrangement 110 provides a constant mass flow stream 112 and a variable flow mass stream 114. The constant mass flow stream 112 is likely to be the greater than the variable mass flow stream 114. The constant flow stream 112 can be varied before testing begins by way of the pressure regulating valve 116. The variable mass flow stream 114 is an extremely fast responding arrangement (15 milliseconds) that receives the signal from the selectable gain circuit 140 and establishes a dilution flow rate relative to engine flow. The quantity of flow from the variable mass flow stream 114 is inversely proportional to the flow rate of the engine 16 (i.e. maximum engine intake flow rate results in proportionally minimum mass flow rate from the variable mass low rate stream 114). In this manner a maximum and proportional rate of sample mass is being extracted from the exhaust stream 48.

An additional benefit is that the transient dilution air flow control arrangement 110 is positioned in close proximity to the partial flow dilution tunnel 38. This reduces the pneumatic capacitance of the gas sampling system 36 and provides for a reaction time of 500 milliseconds or less. In most cases the gas sampling system 36 is capable of reacting within 300 milliseconds or less due to the transient dilution air control arrangement 110.

Other aspects, objects and advantages of this invention can be obtained from a study of the drawings, the disclosure, and the appended claims.

What is claimed is:

1. A gas sampling system for measuring particulate matter in an exhaust gas stream of an internal combustion engine comprising:
    a partial flow dilution tunnel connected to the exhaust gas stream of the engine;
    a first mass flow controller operatively connected an inlet of said partial flow dilution tunnel;
    a second mass flow controller connected to an outlet end of said partial flow dilution tunnel;
    a filter interposed said second mass flow controller and the outlet end of said partial flow dilution tunnel; and
    a transient dilution air control arrangement being interposed the first mass flow controller and the inlet of said partial flow dilution tunnel, said transient dilution air control arrangement includes a constant mass flow stream and a variable mass flow stream non-collinearly connected with said constant mass flow stream prior to the inlet of the partial flow dilution tunnel for controlling a dilution air supply to said partial flow dilution tunnel.

2. The gas sampling system of claim 1, wherein said second mass flow controller is a master controller and the first mass controller is a slave controller.

3. The gas sampling system of claim 1, wherein said transient dilution air control arrangement is positioned in close proximity to said partial flow dilution tunnel.

4. The gas sampling system of claim 1, including a sampling probe being positioned in the exhaust gas stream and the partial flow dilution tunnel.

5. The gas sampling system of claim 1, including a supply of scrubbed and filtered air being connected to said first mass controller.

6. The gas sampling system of claim 1, including a flow measuring device adapted to measure a flow of intake air, said flow measuring device being positioned in a conduit of an air intake of the engine.

7. The gas sampling system of claim 6, wherein said flow measuring device being a laminar flow element, said laminar flow element is connected to a pressure differential transducer to convert pressure differential into an electrical signal.

8. The gas sampling system of claim 7, wherein said pressure differential transducer is connected to a selectable gain circuit.

9. The gas sampling system of claim 8, wherein said selectable gain circuit is switchable to handle one of a single channel input and a multiple channel input.

10. The gas sampling system of claim 8, wherein said selectable gain circuit is selectable between a plurality of coarse settings.

11. The gas sampling system of claim 1, including a vacuum pump connected to said second mass flow controller.

12. The gas sampling system of claim 1, including a solenoid valve connected in parallel with the partial flow dilution tunnel between said first mass flow controller and said partial flow dilution tunnel inlet and said partial flow dilution tunnel outlet and said second mass flow controller.

13. The gas sampling system of claim 1, wherein said constant mass flow stream includes a pressure regulating valve serially connected with a critical flow venturi.

14. The gas sampling system of claim 1, wherein said variable mass flow stream is connected in parallel with said constant mass flow stream.

15. The gas sampling system of claim 1, wherein said variable mass flow stream includes a first pressure regulating valve serially connected with a dome loaded pressure regulating valve and a mass flow transducer.

16. The gas sampling system of claim 15, including a pressure regulating valve serially connected to a voltage to pressure controller.

17. The gas sampling system of claim 16, wherein said voltage to pressure controller is connected to and receives electrical inputs from a flow measuring device and said mass flow transducer, said flow measuring device being adapted to measure a flow of intake air to the engine.

18. The gas sampling system of claim 17, wherein said voltage to pressure controller is connected to and sends pressure signals to said dome loaded pressure regulating valve.

19. The gas sampling system of claim 18, wherein an output from said dome loaded pressure regulating valve is connected down stream of a critical flow venturi of said constant mass flow stream to supply dilution air to said partial flow dilution tunnel.

20. A gas sampling system for measuring particulate matter in an exhaust gas stream of an internal combustion engine comprising:
a partial flow dilution tunnel connected to the exhaust gas stream of the engine;
a first mass flow controller operatively connected an inlet of said partial flow dilution tunnel;
a second mass flow controller connected to an outlet end of said partial flow dilution tunnel;
a filter interposed said second mass flow controller and the outlet end of said partial flow dilution tunnel; and
means for controlling dilution air to said partial flow dilution tunnel, said means being interposed the first mass flow controller and the inlet of said partial flow dilution tunnel, said means includes a constant mass flow stream and a variable mass flow stream non-collinearly connected with said constant mass flow stream prior to the inlet of the partial flow dilution tunnel.

21. The gas sampling system of claim 20, wherein said second mass flow controller is a master controller and the first mass controller is a slave controller.

22. The gas sampling system of claim 20, including a sampling probe being positioned in the exhaust gas stream and the partial flow dilution tunnel.

23. The gas sampling system of claim 22, wherein said sampling probe is a square root extractor.

24. The gas sampling system of claim 20, including a supply of scrubbed and filtered air being connected to said first mass controller.

25. The gas sampling system of claim 20, including a flow measuring device connected to said means for controlling dilution air, said flow measuring device being adapted to measure a flow of intake air, said flow measuring device being positioned in a conduit of an air intake of the engine.

26. The gas sampling system of claim 25, wherein said flow measuring device is a laminar flow element.

27. The gas sampling system of claim 26, wherein said laminar flow element is connected to a pressure differential transducer.

28. The gas sampling system of claim 27, wherein said pressure differential transducer is connected to a selectable gain circuit.

29. The gas sampling system of claim 28, wherein said selectable gain circuit is switchable to handle one of a single channel input and a multiple channel input.

30. The gas sampling system of claim 28, wherein said selectable gain circuit includes a selectable gain switch being selectable between a plurality of coarse voltage positions.

31. The gas sampling system of claim 20, wherein said constant mass flow stream includes a pressure regulating valve serially connected with a critical flow venturi.

32. The gas sampling system of claim 20, wherein said variable mass flow stream is connected in parallel with said constant mass flow stream.

33. The gas sampling system of claim 20, wherein said variable mass flow stream includes a first pressure regulating valve serially connected with a dome loaded pressure regulating valve and a mass flow transducer.

34. The gas sampling system of claim 33, including a pressure regulating valve serially connected to a voltage to pressure controller.

35. The gas sampling system of claim 34, wherein said voltage to pressure controller is connected to and receives electrical inputs from a flow measuring device and said mass flow transducer, said flow measuring device being adapted to measure a flow of intake air to the engine.

36. The gas sampling system of claim 35, wherein said voltage to pressure controller is connected to and sends pressure signals to said dome loaded pressure regulating valve.

37. The gas sampling system of claim 36, wherein an output from said dome loaded pressure regulating valve is connected down stream of a critical flow venturi of said constant mass flowstream to supply dilution air to said partial flow dilution tunnel.

* * * * *